United States Patent [19]

Tonomura et al.

[11] Patent Number: 5,441,667
[45] Date of Patent: Aug. 15, 1995

[54] DETERGENT COMPOSITION

[75] Inventors: Manabu Tonomura, Utsunomiya; Yasushi Kajihara, Kasukabe, both of Japan

[73] Assignee: Kao Corporation, Tokyo, Japan

[21] Appl. No.: 229,100

[22] Filed: Apr. 18, 1994

Related U.S. Application Data

[63] Continuation of Ser. No. 989,937, Dec. 10, 1992, abandoned, which is a continuation of Ser. No. 717,077, Jun. 18, 1991, abandoned.

[30] Foreign Application Priority Data

Jun. 28, 1990 [JP] Japan ................... 2-170882

[51] Int. Cl.$^6$ ................... C11D 3/37; C11D 3/02
[52] U.S. Cl. ................... 252/174.15; 252/174.21; 252/DIG. 5; 252/DIG. 13; 252/174; 424/70.12; 424/78.03; 514/846
[58] Field of Search ............ 424/70, 71, 70.12, 78.03; 252/DIG. 5, DIG. 13, 174.21, 174.15, 174; 514/846

[56] References Cited

U.S. PATENT DOCUMENTS

| | | | |
|---|---|---|---|
| 3,562,786 | 2/1971 | Bailey et al. | 252/174.15 |
| 3,957,970 | 5/1976 | Korkis | 424/70 |
| 5,015,049 | 5/1991 | Yoneyama et al. | 252/174.15 |
| 5,035,832 | 7/1991 | Takamura et al. | 252/174.15 |
| 5,036,108 | 7/1991 | Asahi et al. | 514/937 |

FOREIGN PATENT DOCUMENTS

| | | |
|---|---|---|
| 295886 | 12/1988 | European Pat. Off. . |
| 0331833 | 9/1989 | European Pat. Off. . |
| 331833 | 9/1989 | European Pat. Off. . |
| 373661 | 6/1990 | European Pat. Off. . |
| 2484425 | 6/1980 | France . |
| 2206902 | 1/1989 | United Kingdom . |

*Primary Examiner*—Paul Lieberman
*Assistant Examiner*—Kery A. Fries
*Attorney, Agent, or Firm*—Oblon, Spivak, McClelland, Maier, & Neustadt

[57] ABSTRACT

A detergent composition comprising a polyether-modified silicone having a molecular weight of 3,500 or smaller as a detergent component is disclosed. The detergent composition can effectively eliminate oily residue such as the residues from makeup, e.g. lipsticks, foundations, etc., sebum, and the like in a short period of time, while imparting a pleasant sensation to the skin during and after cleansing.

4 Claims, No Drawings

DETERGENT COMPOSITION

This application is a Continuation-In-Part of application Ser. No. 07/989,937 filed on Dec. 10, 1992, which is a continuation of Ser. No. 07/117,077, filed Jun. 18, 1991, now abandoned.

BACKGROUND OF THE INVENTION

1. Field of the Invention

This invention relates to a detergent composition which can effectively eliminate oily residues such as the residues from makeup, e.g. lipstick, foundation, etc., sebum, and the like in a short period of time, while imparting a pleasant sensation to the skin during and after cleansing.

2. Description of the Background Art

Makeup residue such as the residue from lipstick, foundation, eyeshadow, mascara, and the like which contain a large amount of oil such as solid fats cannot be removed by face cleansing foam containing conventional soaps as a major component, since soaps cannot effectively solubilize or emulsify these oils. For this reason, cleansing creams, cleansing oils, or gel-like cleansing agents which contain an oil base as a major component have been used for removing the makeup residue.

A recent preference is, however, for makeup cosmetics having better adhesiveness to the skin, a higher resistance against water and sebum, and longer makeup retentiveness. A large number of makeup cosmetics for the summer season when large amounts of perspiration are produced use oily solvents such as cyclic silicones as a base component for ensuring a longer makeup retentiveness. Furthermore, various binders, e.g. film-forming polymers, are incorporated in makeup cosmetics to prevent the makeup from running.

Various polymers are also used for hair cosmetics in order to protect the hair or to provide the hair with body.

The residue from these cosmetics, while providing better retentivity and exhibiting an excellent hair protection performance, cannot be removed by conventional cleansers and shampoos. Development of a detergent composition which can effectively remove not only the residue from sebum but also the residue from these makeup cosmetics and hair-protecting agents and which imparts a pleasant sensation during and after cleansing is therefore desired.

SUMMARY OF THE INVENTION

In view of this situation, the present inventors have undertaken extensive studies, and have found that the use of a specific type of low molecular weight polyether-modified silicone as a detergent component produces a detergent composition which exhibits excellent detergency toward makeup residue from summer season cosmetics with a strong retentiveness and provides a pleasant sensation during the cleansing.

Accordingly, an object of this invention is to provide a detergent composition comprising a polyether-modified silicone having a molecular weight of 3,500 or smaller as a detergent component.

As a preferred embodiment, the present invention provides a method of removing residues of make-up cosmetics from the skin which comprises cleansing the skin with a detergent composition comprising a polyether-modified silicone having a molecular weight of 3,500 or smaller as a detergent component.

Other objects, features and advantages of the invention will hereinafter become more readily apparent from the following description.

DETAILED DESCRIPTION OF THE INVENTION AND PREFERRED EMBODIMENTS

Polyether-modified silicone used in the present invention has a molecular weight of 3,500 or smaller, preferably 1,600 or smaller, and most preferably 1,200 or smaller. A preferable HLB value of the polyether-modified silicone is 5–17. Here, the HLB value is defined as the value calculated from cloud value A according to the following equation.

$$HLB = A \times 0.89 + 1.11$$

wherein cloud value A is the amount of 2% aqueous phenol solution (cc) required for the titration of 0.5 gm of an anhydrous sample of polyether-modified silicone dissolved in 5 cc of 98% ethanol at a constant temperature of 25° C.

Given as examples of the polyether-modified silicone are linear or cyclic polyether-modified silicones of the following formula (I).

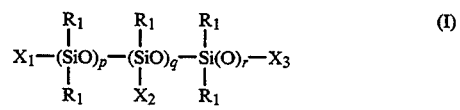

wherein $R_1s$ may be the same or different and each independently represents a methyl or phenyl group, p is a mean value of 0–9, q is a mean value of 1–5, r is 0 or 1, and $X_1$, $X_2$, and $X_3$ may be the same or different and each independently represents a methyl or phenyl group or a group represented by $R_2(OC_3H_6)_b(OC_2H_4)_aO(CH_2)_c$— (wherein $R_2$ is a hydrogen or a lower alkyl group, a is a mean value of 0–16, b is a mean value of 0–12, and c is a number of 1–6, provided that $a+b \geq 1$), or $X_1$ and $X_3$ may form a single bond together, provided that at least one of $X_1$, $X_2$, and $X_3$ is a group represented by $R_2(OC_3H_6)_b(OC_2H_4)_aO(CH_2)_c$—.

Especially preferable polyether-modified silicones are those represented by formula (A)–(D).

A: 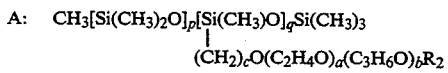

B: 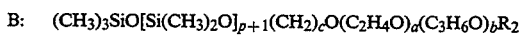

C: 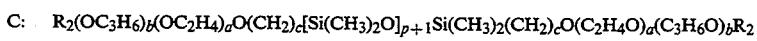

D: 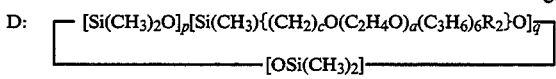

wherein p, q, a, b, c, and $R_2$ are the same as defined above.

Although the polyether-modified silicone of the present invention can be used as a detergent composition as is, it is preferable that it be used as dissolved or dispersed in an aqueous medium. In this instance, the concentration of the polyether-modified silicone in the solution or dispersion is dependent on the intended use of the composition, although a preferable concentration range is 2–60% by weight, and especially preferably 5–30% by weight.

It is desirable that the amount of the above polyether-modified silicone in the total amount of sucrface active components in the composition of the present invention be 50% by weight or more. Accordingly, surface active agents other than polyether-modified silicones can be incorporated in the composition of the present invention as minor detergent components. Such other detergent components may be either nonionic or ionic surface active agents. Given as examples of nonionic surface active agents are glycerine fatty acid esters (e.g. sorbitane fatty acid esters, glycerol monooleate, etc.), sugar fatty acid esters (e.g. sucrose monolaurate, etc.), polyoxyethylene alkyl ethers (e.g. polyoxyethylene lauryl ether, etc.) polyoxyethylene-polyoxypropylene glycol, polyoxyethylene sorbitane fatty acid ester, polyoxyethylene fatty acid ester, alkylalkanol amides, sugar ethers, sugar amides, and the like. Examples of ionic surface active agents which can be used are fatty acid soaps (e.g. potassium laurate) alkyl ether carboxylate (e.g. sodium lauryl ether carboxylate), alkyl sulfate (e.g. sodium lauryl sulfate), polyoxyethylene alkyl ether sulfate, alkyl phosphate (e.g. sodium monolauryl phosphate), N-acylamino surface active agents (e.g. sodium lauroyl-N-methyl taurine, sodium N-lauroyl-L-glutamate), sulfo-succinic acid surface active agent, imidazoline surface active agents (e.g. Miranol, Softazoline), betaine compounds (e.g. laurylacetic acid betaine), amine oxides, and the like.

In addition to the above components, other components can optionally be incorporated in the detergent composition of the present invention as required. Such optional components include alcohols, water, liquid oils, fatty acids, pharmaceutically active components, moisturizing agents, anti-inflammation agents, antiseptics, preservatives, UV ray absorbers, antioxidants, viscosity increasing agents, organic and inorganic powders, pigments, perfumes, and the like. The detergent composition can be made into any desired form, including liquid and gel. It is preferable that the detergent composition of the present invention be used as aqueous-type products, not emulsion-type products in which a large amount of oil is incorporated.

The detergent composition of the present invention can be prepared by blending the above components by a conventional method. The product can directly be applied to the hair or the skin, and after massaging, can be washed out with water.

The detergent composition of the present invention can effectively eliminate in a short period of time the residue from the makeup for use in the summer season which has good makeup retentivity and thus is hard to remove. It imparts a pleasant sensation after cleansing. It can be used under the conditions where conventional jelly type cleansers could not properly be used, i.e. under conditions where the skin is wet with water, e.g. in a bath room.

Other features of the invention will become apparent in the course of the following description of the exemplary embodiments which are given for illustration of the invention and are not intended to be limiting thereof.

EXAMPLES

Example 1

Detergent compositions listed in Table 1 were prepared to evaluate their detergency toward a water-resistant foundation having the following formulation.
Formulation of the Water-resistant Foundation

|  | % by weight |
| --- | --- |
| High molecular weight silicone (M.W. 3,000) | 5.0 |
| Cyclic silicone (Si = 5) | 27.0 |
| Polyether-modified silicone (M.W. 3,500) | 3.0 |
| Squalane | 15.0 |
| Candellila wax | 3.0 |
| Perfume | 0.1 |
| Ion-exchanged water | 0.9 |
| Sericite | 15.0 |
| Nylon powder | 15.0 |
| Titanium oxide | 13.0 |
| Iron oxide | 3.0 |
| Total | 100.0 |

The foundation was applied to several sites of about 2 cm diameter in the forearms of the panelists and left for one hour before washing to completely dry.

One or two drops of the sample detergent compositions were dropped onto the sites and immediately spread by massaging the site with the fingers at about 100 gm pressure for 10 minutes, twice per minute. Immediately after the massaging, the site was again rubbed with fingers wetted with tap water for 5 seconds, twice per second. Then, the materials on the skin were washed out with a stream of water while rubbing for 5 seconds, twice per second.
Evaluation
(1) Detergency The test sites of the forearms were observed by the panelists with the naked eye during and after washing. The results were grouped into the following four grades.

AAA: The foundation immediately dissolved almost completely with no residue remaining.
BBB: The foundation dissolved not immediately but gradually. No residue remained ultimately.
CCC: Removal of the foundation could be observed, but some residue remained ultimately.
DDD: The foundation was removed with difficulty. The results were the same as the case where the site was simply washed with water.

(2) Sensation Upon Use

The sensation imparted to the skin during and after washing was evaluated by the 5 panelists. Sensation during use was evaluated in terms of the spreadability of the sample detergent composition over the skin. Sensation after washing was judged to be good if a moistened, fresh sensation was imparted, and to be bad if a creaky, sticky, oily, or slippery sensation was imparted. The results were grouped into 3 grades.

AAA: The sensation was good or no change in sensation was felt.
BBB: Sensation was bad.
CCC: The sensation was to bad to tolerate.

(3) The results are shown in Table 1.

TABLE 1

| Component | Invention Product | | | | Comparative Product | | | | |
|---|---|---|---|---|---|---|---|---|---|
| | 1 | 2 | 3 | 4 | 1 | 2 | 3 | 4 | 5 |
| Polyether-modified silicone A *1 | 20 | 20 | 20 | 15 | — | — | — | — | — |
| Polyether-modified silicone B *2 | — | — | — | — | 20 | — | — | — | — |
| Sodium stearate | — | 5 | — | — | — | 10 | — | — | — |
| Polyoxyethylene lauryl ether *3 | — | — | — | — | — | — | 20 | — | — |
| Polyoxyethylene-sec-tetradecyl ether *4 | — | — | — | — | — | — | — | 20 | — |
| Sodium N-lauroyl-L-glutamate *5 | — | — | 10 | 20 | — | — | — | — | 20 |
| Water | Balance | | | | | | | | |
| <Evaluation> | | | | | | | | | |
| Detergency | AAA | BBB | AAA | AAA | DDD | DDD | CCC | CCC | CCC |
| Sensation | AAA | AAA | AAA | AAA | CCC | CCC | BBB | BBB | BBB |

1m0.5"
*1 Polyether-modified silicone A (a compound of formula A, MW = 600, HLB = 12, manufactured by Nippon Uniker)
*2 Polyether-modified silicone B (a compound of formula A, MW = 4500, HLB = 10, manufactured by Sin-etsu Chemical)
*3 Emulgen 105
*4 Softanol 33
*5 Amisoft LS-11

Example 2

50% aqueous solutions of the polyether-modified silicones listed in Table 2 were prepared to evaluate their detergency toward a summer season foundation and their sensation imparted upon use in the same manner as in Example 1. The results are shown in Table 2.

TABLE 2

| | Polyether-modified silicone | | | Evaluation | |
|---|---|---|---|---|---|
| | Symbol | M.W. | HBL | Detergency | Sensation |
| Invention Product | | | | | |
| 5 | A | 600 | 12 | AAA | AAA |
| 6 | C | 700 | 12 | AAA | AAA |
| 7 | D | 780 | 17 | AAA | AAA |
| 8 | E | 850 | 13 | AAA | AAA |
| 9 | F | 1,000 | 12 | AAA | AAA |
| Comparative Product | | | | | |
| 6 | G | 4,000 | 14 | DDD | DDD |
| 7 | B | 4,000 | 10 | DDD | DDD |
| 8 | H | 8,000 | 7 | DDD | DDD |
| 9 | I | 11,000 | 7 | DDD | DDD |
| 10 | J | 20,000 | 18 | DDD | DDD |

Polyether-modified silicones
A, B Same polyether-modified silicones as in Example 1
C: a compound of formula A, manufactured by Shin-etsu Chemical)
D: a compound of formula A, manufactured by Shin-etsu Chemical)
E: a compound of formula A, manufactured by Shin-etsu Chemical)
F: a compound of formula A, manufactured by Shin-etsu Chemical)
G: a compound of formula A, manufactured by Shin-etsu Chemical)
H: a compound of formula A, manufactured by Shin-etsu Chemical)
I: a compound of formula A, manufactured by Shin-etsu Chemical)
J: a compound of formula A, manufactured by Shin-etsu Chemical)

Example 3

A composition for removing the residue of make-up was prepared.
Formulation

| | % by weight |
|---|---|
| Polyether-modified silicone F | 10.0 |

-continued

| | % by weight |
|---|---|
| Polyoxyethylene isocetyl ether | 10.0 |
| Ethylcarbitol | 15.0 |
| Glycerol | 10.0 |
| Carageenan | 0.5 |
| Ion-exchanged water | Balance |
| | 100.0 |

The above agent was used for removing the residue of make-up (a summer season foundation) exhibiting an excellent removing effect while giving a good feeling upon use.

Example 4

A composition for removing the residue of make-up was prepared.
Formulation

| | % by weight |
|---|---|
| Polyether-modified silicone F | 15.0 |
| Lauryldimethylamino acetate betain | 10.0 |
| Polyacryl (Carbopole 941) | 0.5 |
| Ion-exchanged water | Balance |
| (Adjusted to pH 7.0 with 0.1N NaOH) | |
| | 100.0 |

The above agent was used for removing the residue of make-up (a summer season, foundation) exhibiting an excellent removing effect while giving a good feeling upon use.

Obviously, numerous modifications and variations of the present invention are possible in light of the above teachings. It is therefore to be understood that within the scope of the appended claims, the invention may be practiced otherwise than as specifically described herein.

What is claimed is:

1. An aqueous, non-emulsion skin cleansing composition consisting essentially of
(A) 5 to 30 wt. % of a polyether-modified silicone, having a molecular weight of 1600 or smaller and an HLB value of 5-17, represented by the following formula (I):

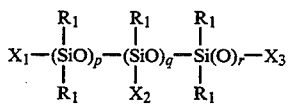

wherein $R_1$s may be the same or different and each independently represents a methyl or phenyl group, p is a mean value of 0–9, q is a mean value of 1–5, r is 0 or 1, and $X_1$, $X_2$, and $X_3$ may be the same or different and each independently represents a methyl or phenyl group or a group $R_2(OC_3H_6)_b(OC_2H_4)_aO(CH_2)_c$— wherein $R_2$ is a hydrogen or a lower alkyl group, a is a mean value of 0–16, b is a mean value of 0–12, and c is a number of 1–6, provided that $a+b \geq 1$, or $X_1$ and $X_3$ may form a single bond together, provided that at least one of $X_1$, $X_2$, and $X_3$ is a group $R_2(OC_3H_6)_b(OC_2H_4)_aO(CH_2)_c$—, (B) a nonionic or ionic surface active agent, and
(C) water, wherein the ratio of (A) to (B) is equal to or larger than 1.

2. The skin cleansing composition according to claim 1, wherein said polyether-modified silicone is a compound selected from polyether-modified silicones represented by formula (A), (B), (C), or (D):

A: $CH_3[Si(CH_3)_2O]_p[Si(CH_3)O]_qSi(CH_3)_3$
  $\quad\quad\quad\quad\quad\quad\quad\quad |$
  $\quad\quad\quad\quad\quad (CH_2)_cO(C_2H_4O)_a(C_3H_6O)_bR_2$ B: $(CH_3)_3SiO[Si(CH_3)_2O]_{p+1}(CH_2)_cO(C_2H_4O)_a(C_3H_6O)_bR_2$ C: $R_2(OC_3H_6)_b(OC_2H_4)_aO(CH_2)_c[Si(CH_3)_2O]_{p+1}Si(CH_3)_2(CH_2)_cO(C_2H_4O)_a(C_3H_6O)_bR_2$ D: $\Big[ [Si(CH_3)_2O]_p[Si(CH_3)\{(CH_2)_cO(C_2H_4O)_a(C_3H_6)_6R_2\}O]_{\overline{q}}\Big.$
  $\Big.\quad\quad\quad\quad\quad\quad\quad [OSi(CH_3)_2] \quad\quad\quad\quad\quad\quad\quad \Big]$ wherein p is a mean value of 0–9, q is a mean value of 1–5, $R_2$ is a hydrogen or a lower alkyl group, a is a mean value of 0–16, b is a mean value of 0–12, and c is a number of 1–6, provided that $a+b \geq 1$.

3. A method of removing residues of make-up cosmetics from the skin which comprises cleansing the skin with an aqueous, non-emulsion skin cleansing composition consisting essentially of (A) 5 to 30 wt. % of a polyether-modified silicone, having a molecular weight of 1600 or smaller and an HLB value of 5–17, represented by the following formula (I):

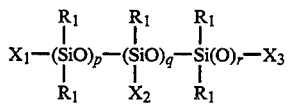

wherein $R_1$s may be the same or different and each independently represents a methyl or phenyl group, p is a mean value of 0–9, q is a mean value of 1–5, r is 0 or 1, and $X_1$, $X_2$, and $X_3$ may be the same or different and each independently represents a methyl or phenyl group or a group $R_2(OC_3H_6)_b(OC_2H_4)_aO(CH_2)_c$— wherein $R_2$ is a hydrogen or a lower alkyl group, a is a mean value of 0–16, b is a mean value of 0–12, and c is a number of 1–6, provided that $a+b \geq 1$, or $X_1$ and $X_3$ may form a single bond together, provided that at least one of $X_1$, $X_2$, and $X_3$ is a group $R_2(OC_3H_6)_b(OC_2H_4)_aO(CH_2)_c$—, (B) a nonionic or ionic surface active agent, and
(C) water, wherein the ratio of (A) to (B) is equal to or larger than 1.

4. The method according to claim 3, wherein said skin cleansing composition is applied to the skin, and after massaging, is washed out with water.

* * * * *

UNITED STATES PATENT AND TRADEMARK OFFICE
CERTIFICATE OF CORRECTION

PATENT NO. : 5,441,667
DATED : August 15, 1995
INVENTOR(S) : Manabu TONOMURA, et al.

It is certified that error appears in the above-indentified patent and that said Letters Patent is hereby corrected as shown below:

On the title page, Item [54] and Column 1, Lines 2 and 3, the title should read:

--AQUEOUS, NON-EMULSION SKIN CLEANSING COMPOSITION OF A POLYETHER MODIFIED SILICONE--

Signed and Sealed this

Seventeenth Day of October, 1995

*Attest:*

BRUCE LEHMAN

*Attesting Officer*  *Commissioner of Patents and Trademarks*